(12) United States Patent
Pletser et al.

(10) Patent No.: US 6,658,369 B2
(45) Date of Patent: Dec. 2, 2003

(54) METHOD AND DEVICE FOR THE PREDICTIVE DETERMINATION OF A PARAMETER REPRESENTATIVE OF THE MENTAL ACTIVITY OF A PERSON

(76) Inventors: Vladimir Pletser, Storm van's-Gravensandeweg 101, NL-2242 JE Wassenaar (NL); Olga Quadens, Avenue Altertyn, 14, B-1200 Bruxelles (BE)

( * ) Notice: Subject to any disclaimer, the term of this patent is extended or adjusted under 35 U.S.C. 154(b) by 136 days.

(21) Appl. No.: 09/933,471

(22) Filed: Jul. 27, 2001

(65) Prior Publication Data

US 2002/0042691 A1 Apr. 11, 2002

(30) Foreign Application Priority Data

Aug. 4, 2000 (FR) .............................................. 00 10335

(51) Int. Cl.$^7$ ................................................. G06F 9/04
(52) U.S. Cl. ...................... 702/181; 702/179; 702/180; 702/182; 702/183
(58) Field of Search .............................. 702/19, 32, 33, 702/189, 179–183; 600/300, 544, 387; 514/12, 251; 435/23.1, 6; 607/45

(56) References Cited

U.S. PATENT DOCUMENTS

| 5,467,777 | A | * | 11/1995 | Farwell ....................... 128/731 |
| 5,857,978 | A | | 1/1999 | Hively et al. ................ 600/544 |
| 6,419,629 | B1 | * | 7/2002 | Balkin et al. ................ 600/300 |
| 6,496,724 | B1 | * | 12/2002 | Levendowski et al. ...... 600/544 |
| 6,511,424 | B1 | * | 1/2003 | Moore-Ede et al. ......... 600/300 |

OTHER PUBLICATIONS

Theiler J. et al: "Re-examination of the evidence for low-dimensional, non-linear structure in the human electroencephalogram" Electroencephalography and Clinical Neurophysiology, Mar. 1996, Elsevier, Ireland, vol. 98, No. 3, pp. 213–222.

Pijn J P et al: "Chaos or noise in EEG signals; dependence on state and brain site" Electroencephalography and clinical Neurophysiology, Nov. 1991, Ireland, vol. 79, No. 5, pp 371–381.

Pezard et al. "Non-linear forecasting measurements of multichannel EEG dynamics" Electroencephalography and clinical Neurophysiology, Nov. 1994, Ireland, vol. 91, No. 5, pp. 383–391.

Soong et al.—"Evidence of Chaotic Dynamics Underlying the Human Alpha–Rhythm Electroencephalogram" Biological Cybernetics, DE, Springer Verlag, Heidelberg, vol. 62, No. 1, Nov. 1, 1989, pp. 55–62.

* cited by examiner

Primary Examiner—Marc S. Hoff
Assistant Examiner—Felix Suarez
(74) Attorney, Agent, or Firm—Dickinson Wright PLLC (57) ABSTRACT

The invention relates to the method for the predictive determination of a parameter representative of the mental activity of a person, which method involves:

A) the acquisition of encephalograms of said person in the course of at least two exertion sequences separated by a rest sequence;

B) the calculation in the course of each of said exertion sequences of the mean value of the dimension of a chaotic attractor, denoted $d_f(t)$;

C) the calculation for said exertion sequences and said rest sequence of a fatigue function F(t) and of a recovery function R(t) according to an exponential mode, with:

$$F(t) = F_0\, e^{-ft}$$

$$R(t) = R_0\, e^{rt}$$

f and r denoting a fatigue coefficient and rest coefficient respectively;

D) making a prediction of the changes in the dimension d, defined by df(t)=E(t)R(t) in the course of at least two exertion sequences separated by a period of rest.

18 Claims, 4 Drawing Sheets

METHOD AND DEVICE FOR THE PREDICTIVE DETERMINATION OF A PARAMETER REPRESENTATIVE OF THE MENTAL ACTIVITY OF A PERSON

The subject of the present invention is a method and a device for the predictive determination of a parameter representing the changes in the mental activity of a person who performs work in the form of one or more exertion sequences, with at least one rest sequence.

In the past, studies have been carried out on the basis of EEG electroencephalograms of several people, charted in the course of series of parabolic flights organized by the EUROPEAN SPACE AGENCY.

These EEG data have been processed by the method of dimensions of singular attractors or strange attractors or chaotic attractors, in which method correlation functions C (r) for the attractor are calculated from EEG data The slope of the linearized curves of log C (r) versus log r gives the correlation dimensions d of the attractors Reference may be made in particular to the article by K. de Metz and colleagues entitled <<Quantified EEG in different C situations>>, published in Acta Astronautica vol. 32, No. 2—1994, pages 151–157, and more particularly on page 155 and in FIG. 4 of this article.

This article itself refers to an article by A. Babloyants and colleagues, entitled <<Evidence of chaotic dynamics of brain activity during the sleep cycle>> and published in September 1985 in Physics Letters, vol. 111A, No. 3, pages 152 to 156 (Elsevier Science Publishers B.V.).

Reference may also be made to the more recent article by E. Basar and R. Quian Quiroya, which constitutes chapter 10<<Chaos in Brain Function>> of the work <<Brain Function and Oscillations>> (vol. 1: Brain Oscillations, Principles and Approaches).

The carrying out of complicated missions, for example the missions of astronauts, makes it desirable to be able to forecast whether a given person is able to fulfill a mission, in the course of which, phases of work alternate with phases of rest to be observed, whilst maintaining satisfactory mental availability.

The basic idea of the present invention is that the dimension d up to a value of less than 10 is representative of the mental activity of a person, a high value of d indicating high mental availability and a low value of d possibly representing low mental availability, or even a state of fatigue, and that analysis of this dimension is capable of leading to the implementation of a prediction.

The invention thus relates to a method for the predictive determination of a parameter representative of the mental activity of a person, which method involves:

A) the acquisition of encephalograms of said person in the course of at least two exertion sequences separated by a rest sequence;

B) the calculation in the course of each of said exertion sequences of the mean value of the dimension of a chaotic attractor, denoted $d_j(t)$;

C) the calculation for at least said exertion sequence and said rest sequence of a fatigue function F(t) and of a recovery function R(t) according to an exponential mode, with:

$F(t)=Fo\ e^{-ft}$ $R(t)=Ro\ e^{rt}$ f and r denoting positive coefficients of fatigue and of rest respectively;

D) a prediction of the value of the dimension d defined by the product of the fatigue and recovery functions with df(t)=F(t)R(t), for at least two successive exertion sequences having a first and a second durations alternating with at least one period of rest having a third duration.

The method can involve at least two exertion sequences of different intensity and the determination of fatigue coefficients f1, f2, . . . corresponding to each of said sequences.

The making of a prediction is carried out by linearly approximating at least one fatigue function and/or the recovery function.

The making of a prediction can be carried out by comparing at least one fatigue function with the corresponding recovery function.

Preferably, in B, the calculation is carried out in respect of EEG encephalograms gathered in time intervals corresponding to exertion sequences and by subsequently comparing them with the EEG encephalograms corresponding to sequences in the course of which said person is not subjected to this exertion.

According to a preferred mode of implementation, the method is one wherein the making of a prediction involves optimizing the duration of at least one exertion sequence and/or of at least one rest sequence so that after a given time interval, in the course of which several exertion sequences have been carried out, the set of which corresponds to one and the same aggregate exertion alternating with rest sequences, the final value of the dimension d is as large as possible.

The invention also relates to a device for the predictive determination of a parameter representative of the mental activity of a person, which device comprises a module for acquiring encephalographic data;

a module for calculating the dimension of a chaotic attractor, from predefined encephalographic data series;

a module for calculating at least one fatigue coefficient and a rest coefficient from a time-dependent exponential model of the changes in said dimension;

a module for predicting the value of the dimension d for a sequence exhibiting at least two periods of exertion having a first and a second durations separated by a period of rest having a third duration.

The second calculation unit can have a means of calculating various fatigue coefficients f1, f2, . . . associated with exertion sequences of different intensity.

The prediction unit can have a subunit making it possible to linearly approximate at least one fatigue function and/or a recovery function. According to a preferred mode of implementation, the device is one which has an optimization unit making it possible to optimize the duration of at least one exertion sequence and/or of at least one rest sequence so that after a predetermined time interval, in the course of which several exertion sequences have been carried out, the set of which corresponds to one and the same aggregate exertion, alternating with rest sequences, the final value of the dimension d is as large as possible.

The invention will be better understood on reading the description which follows, in conjunction with the drawings in which.

To create a microgravity environment, parabolic flights are carried out, by way of example, with the aid of a specially rigged aircraft. For the tests mentioned below, an aircraft of the <<Caravelle>> type was used from the Brótigny Flight Trials Center base.

Figure 1:
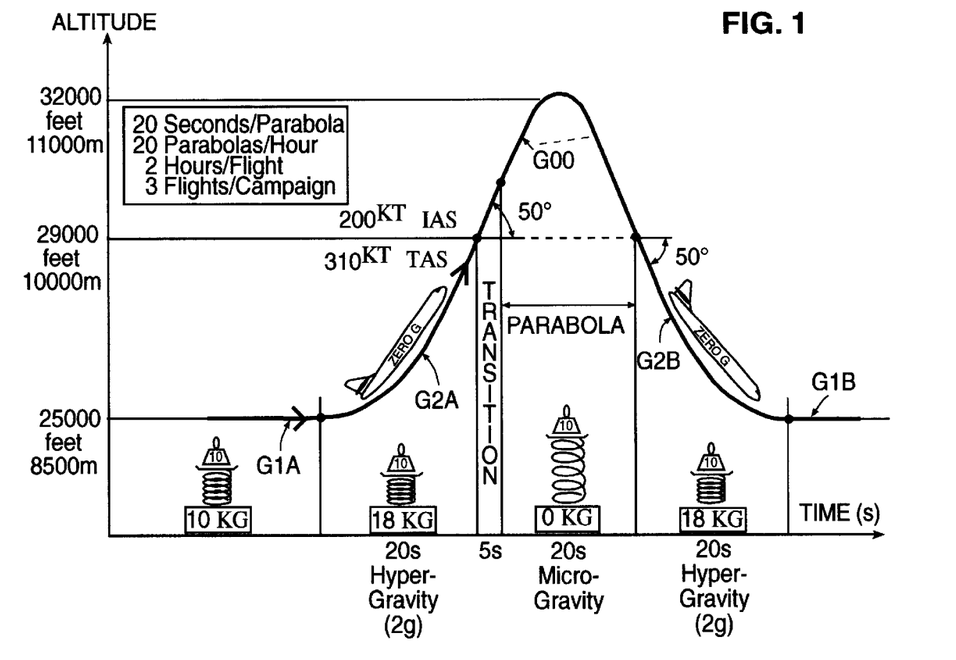
FIG. 1 illustrates a parabolic flight broken down into its various phases.

A parabolic flight, illustrated in FIG. 1, exhibits five phases:

a phase G1A of horizontal flight G1A at an altitude of 8 000 m;

a phase G2A of climbing flight (around 20 s) at an angle of 50° from 8 to 10 000 m;

a phase G00 of flight along a parabolic trajectory (20 to 25 s) without acceleration, between 10 000 and 11 000 m and then 11 000 m and 10 000 m, in the course of which the aircraft experiences microgravity conditions;

a phase G2B of descent (around 20 s) at an angle of 50° from 10 000 to 8 000 m;

a phase G1B of horizontal flight at an altitude of 8 000 m.

The parabolic flights are separated by intervals of 2 to 6 minutes.

A flight (F1, F2, . . . ) lasts two and a half hours in the course of which some thirty parabolic maneuvers are carried out.

A campaign involves three flights F1, F2, F3 lasting two and a half hours and separated by rest intervals, which in the test, were 30 hours between the first F1 and the second F2 flights, and 18 hours between the second F2 and the third F3 flights By way of example, the value of the dimension d such as defined in the aforesaid article by K. de Metz and colleagues was measured in the course of a campaign of three flights of two and a half hours.

Each of the flights was broken down into three time periods corresponding to the start, middle and end of each of the flights.

Figure 2A:
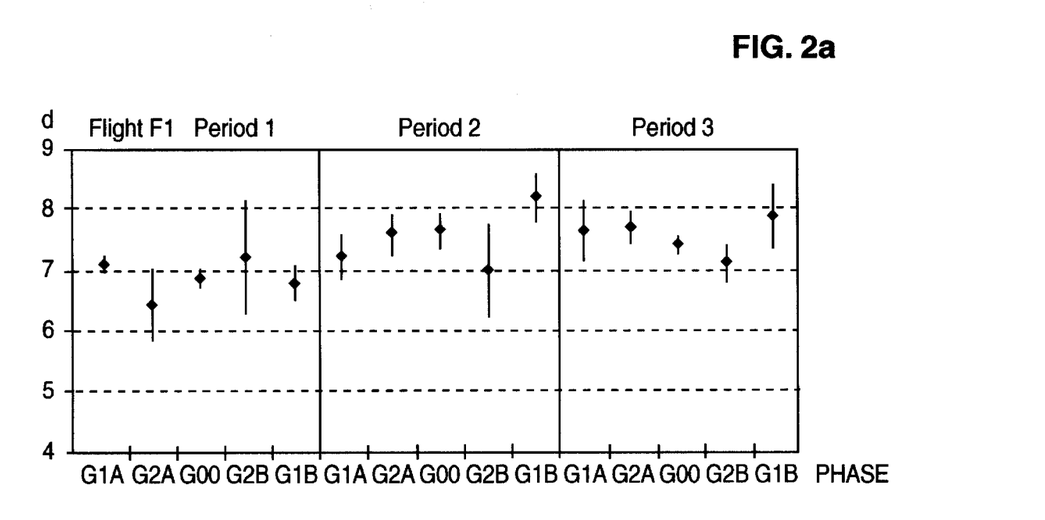
FIGS. 2a to 2c give mean values of the dimension d of the singular attractor in the course of each of the phases G1A, G2A, G00, G2B, G1B of each of the periods of each flight F1 to F3, FIG. 2d summarizing the mean values of d for each of the phases of each of the flights F1 to F3.

For the first flight F1, the mean values of d measured in the course of phases G1A, G2A, G00, G2B and G1B were respectively 7.13, 6.44, 6.91, 7.20 and 6.76 (i.e. between 6.44 and 7.20) for the first period, 7.22, 7.58, 7.61, 7.08 and 8.17 (i.e. between 7.08 and 8.17) for the second period and 7.61, 7.69, 7.39, 7.12 and 7.82 (i e. between 7.12 and 7.82) for the third period (FIG. 2a).

Figure 2B:
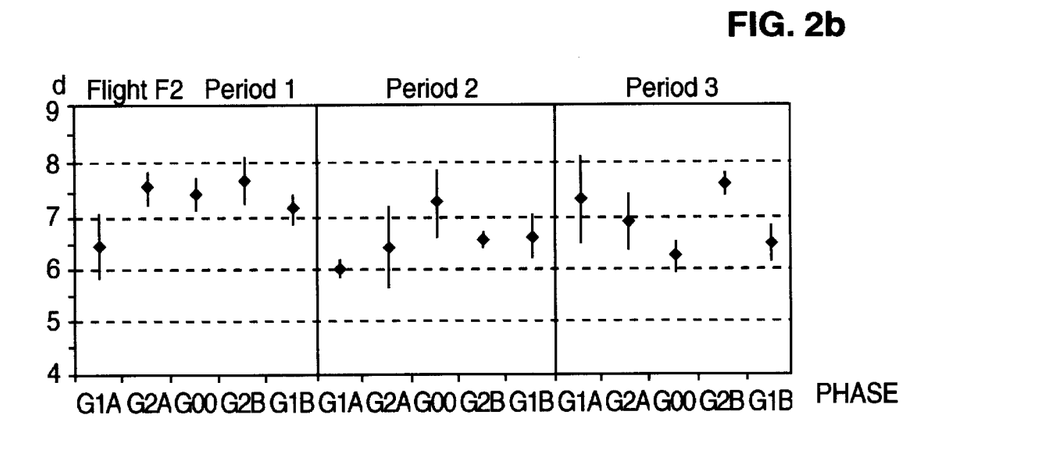

For the second flight F2, the mean values of d varied between 6.50 and 7.68 for the first period, between 6.02 and 7.25 for the second period, and between 6.19 and 7.51 for the third period (FIG. 2b).

Figure 2C:
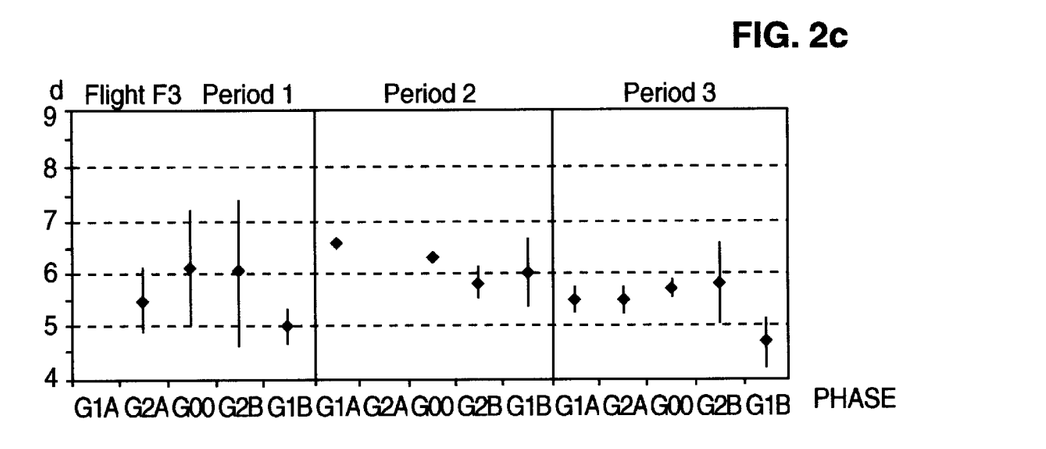

For the third flight E3, the mean values of d varied between 5.00 and 6.10 for the first period, between 5.84 and 6.61 for the second period, and between 4.61 and 5.76 for the third period (FIG. 2c).

Figure 2D:
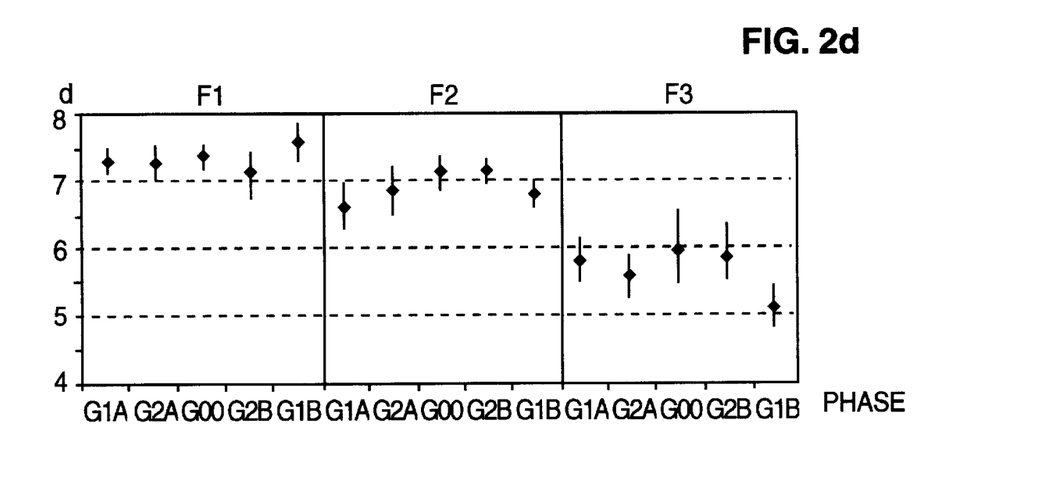

For each of the three flights as a whole, the mean values of d varied between 7.27 and 7.59 for the first flight, between 6.60 and 7.15 for the second flight, and between 5.06 and 5.95 for the third flight (FIG. 2d).

It was possible to demonstrate the influence of gravity alone by combining the mean values recorded during periods at 1 g (G1A and G1B) at 2 g (G2A and G2B) and in microgravity (G00).

The results are shown in FIG. 2c.

We have:

d=6.73±0.15 at 2 g d=6.63±0.15 at 1 g d=6.79±0.25 at 0 g.

The variations about these mean values are too large to be conclusive and another parameter must be considered in order Lo analyze the individual variations of d over time. This other parameter is the fatigue aggregated over time during the three flights and which must be separated into short-term fatigue (during a parabola) and long-term fatigue (from one flight to another).

The phases G1A will be considered subsequently insofar as they describe the activity of the brain during an exertion sequence, but at a moment at which the exertion is not accomplished, that is to say a state of relative rest of the brain during a phase of exertion. These data are regarded as more representative and more reproducible than those logged during a state of non-rest or during exertion (microgravity or acceleration or deceleration of 2 G), since the alpha waves of the brain are more stable.

Figure 3:
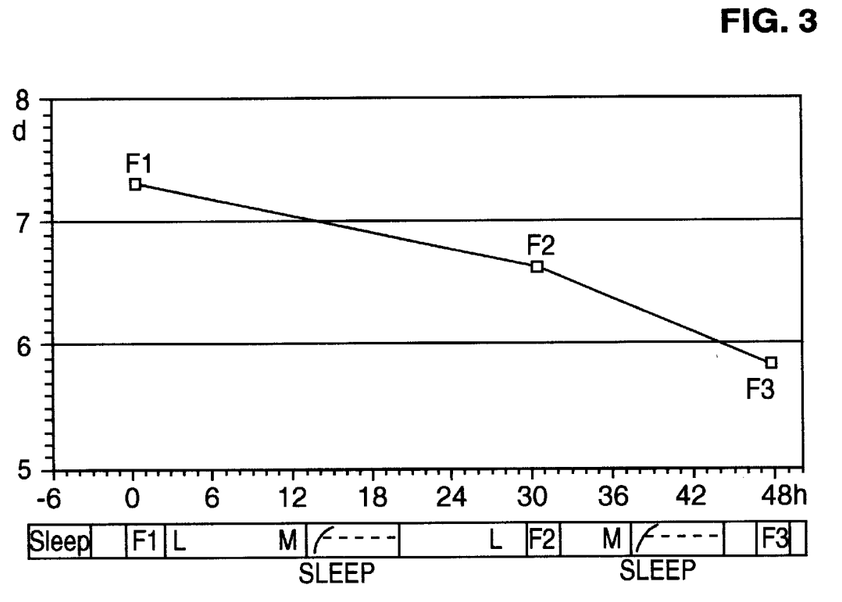
FIG. 3 is the curve of the mean value of d taken within phase G1A, for each of the flights F1 to F3.

To represent the mean state of the brain activity of the subject before each flight, the mean value of d in a normal environment at 1 g is approximated by the mean of the values of d as calculated over the set of phases G1A of each flight, this giving 7.31 for the first flight, 6.60 for the second flight and 5.57 for the third flight (see FIG. 3). These three values are taken as the values of d representing the mean brain state of the subject at 1 g before each flight A decrease $$\left(\frac{\Delta d}{\Delta t}\right)_{3-1} = -0.024 \text{ d/h}$$

is observed between the first F1 and the second F2 flights, h denoting the time in hours.

A decrease $$\left(\frac{\Delta d}{tr}\right)_{3-1} = -0.048 \text{ d/h}$$

is observed between the second F2 and the third F3 flights, this decrease corresponding to twice the value noted between flights 1 and 2, and a decrease $$\left(\frac{\Delta d}{\Delta t}\right)_{3-1} = -0.033 \text{ d/h}$$

between the first F1 and the third F3 flights

These decreases correspond to relative decreases Δd/d of 0.1 between flights F1 and F2, of 0.125 between flights F2 and F3 and of 0.21 between flights F1 and F3, i.e. relative decreases [(Δd/Δd)/t] of 1% in 3 hours (10% in 30 hours) between flights F1 and F2, of 1% in 1h30 (12.5% in 17.5 hours) between flights F2 and F3 and of 1% in 2h15 (21% in 47 hours) between flights F1 and F3.

The relative decrease in the values of the dimension d for the sequences at 1 g is, between flights F2 and F3, twice what it is between flights F1 and F2.

In the course of the first flight, 20 minutes were spent at an acceleration of 2 g, but this has little influence on the mean values of d taken for the values at 1 g.

By contrast the aggregate fatigue due to the first flight F1 has an influence on the value of d in the course of the sequences at 1 g in the course of the second flight F2 (d=6.5 at the start of the second flight) and remains close to the mean value of d (6.6) calculated in the course of the second flight.

The relative decrease in d is only 1% per period of 3 hours between flights F1 and F2.

In the course of the third flight F3, the accumulation of 40 minutes at 2 g due to the first two flights F1 and F2, as well as the reduced recovery time between flights F2 and F3 (less than 18 hours) leads to a value of d at 1 g of 5.77 in the course of the third flight F3 The relative decrease in the value at 1 g is around 1% in 1.30 hours between flights F2 and F3, this corresponding to twice that noted between flights F1 and F2.

This observation confirms in a surprising manner the assumption that the application of two 20 minute periods in an environment at 2 g leads to a drop in the mean value d measured in the course of a sequence at 1 g which is twice that which is observed after implementing a single cumulative period of 20 minutes in an environment at 2 g.

The straight line which joins the two mean values of d in the course of the first flight F1 and of the second flight F2 may be regarded as satisfying the following equation (see FIG. 3):

$$d_{1-2}=7.312-0.024t$$

where t is expressed in hours.

Figure 4:
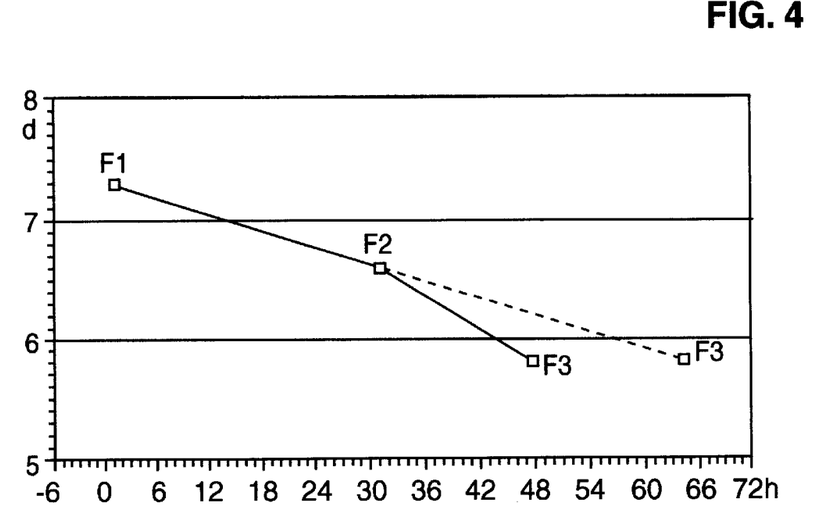
FIG. 4 illustrates an extrapolation arising from this curve.

If one wishes this straight line to extend in such a way that the slope remains the same (1% of decrease every 3 hours instead of every 1.5 hours), an additional recovery time of 16.5 hours must be allowed for between the second F2 and third F3 flights, this corresponding to a total rest time of 34 hours between flights F2 and F3, i.e. 64.5 hours after the start of flight F1 (see FIG. 4). With the same rates of decrease, if the second flight had taken place on the morning of the second day at the same time as the first flight on the previous day, that is to say 6 hours earlier, it would have been possible to observe a value of 6.74 instead of 6.60 for the second flight F2. By advancing the second flight by 6 hours, the recovery time between flights F2 and F3 is correspondingly increased.

The problem is to model the calculation of the value at 1 g in the course of the third flight F3.

To calculate the rest time necessary between two flights, it is necessary to be able to determine the rate r(t) of recovery as a function of time which corresponds to a natural re-increase in the value of d allowed by rest after a period of fatigue accumulated in the course of a flight lasting two and a half hours.

Accordingly, the actual behavior is regarded as resulting from the competition between two antagonistic processes, namely on the one hand, the accumulated fatigue (due essentially to the periods at 2 g) which tends to lower the value of d and, on the other hand, the recovery process due to rest and which commences as soon as a flight (F1, F2, etc.) ends, with little effect at the start, this effect increasing over time.

The form of the decreases in d which are observed between two consecutive flights F1, F2 or F2, F3, suggests that the two fatigue and recovery processes may be represented by exponential functions, namely, F(t) for fatigue and R(t) for recovery, with:

$$F(t)=Fo\ e^{-ft}$$

$$R(t)=Ro\ e^{rt}$$

f and r denote the (positive) rates of fatigue and of rest, Fo and Ro being constants at the instant t=0.

The variation over time of the value of d is then represented by:

$$d=F(t)R(t)=Do\ e^{(r-f)t}$$

with Do=FoRo and f>r.

Specifically, the fatigue constant f is necessarily greater than the recovery constant r on account of the negative slope of the curve.

By applying this relation to the first part of the curve of FIG. 3, which corresponds to the interval between flights F1 and F2, we obtain:

$$d1=Do$$

$$d2=Do\ e^{(r-f)(t2-t1)}$$

hence:

$$d1-d2=d1[1-e^{(r-f)(t2-t1)}]$$

where $t_1$ and $t_2$ are mean times representing the start of flights F1 and F2 respectively.

By applying this same relation to the second part of the curve of FIG. 3, which corresponds to the interval between flights F2 and F3, we obtain $$d2=D'o$$

$$d3=D'o\ e^{(r-f)(L3-L2)}$$

$$d2-d3=d2\ [1-e^{(r-f)(L3-L2)}]$$

where $t_2$ and $t_3$ are mean times representing the start of flights F2 and F3 respectively.

The second flight F2 being identical to the first flight F1, the rate of fatigue f' between the second F2 and third F3 flights is regarded as twice the rate of fatigue f between the first F1 and second F2 flights, since the rate of fatigue f' is due mainly to the application of two aggregate periods of 2 g in the course of the first two flights (f'=2f):

$$F(t)=F'o\ e^{-ft}e^{-ft}$$

hence f'=2f.

By linear approximation of the exponential function, we have:

$$r-t=-0.024/d1$$

$$r-2f=-0.048/d2$$

hence $$f=4\times10^{-3}h^{-1}$$

$$r=7.06\times10^{-4}h^{-1}$$

i.e. a fatigue rate 6 Limes greater than the recovery rate.

The equation system can be solved without resorting to a linear approximation.

We then have:

$$\log(d2/d1)/(t2-t1)=r-f$$

$$\log(d3/d2)/(t3-t2)=r-2f$$

log denoting the Napierian logarithm.

We then have:

$$f=4.3 \times 10^{-3}$$

and $$r=8.7 \times 10^{-4}.$$

With this model, the decrease in d after Δt=24 hours is:

$$e^{(r-f)\Delta t}=0.921$$

between the first F1 and the second F2 flight
and $$e^{(r-2f)\Delta t}=0.831$$

between the second F2 and the third F3 flight.
We then obtain:

$$(d1-d2)/d1=1-e^{(r-f)\Delta t}=0.079 \text{ between F1 and F2}$$

$$(d2-d3)/d2=1-e^{(r-2f)\Delta t}=0.169 \text{ between F2 and F3}$$

and the relative decreases:
of 7.9% in 24 hours, i.e. 1% in 3 hours between F1 and F2,
of 16.9% in 24 hours, i.e. 1% in 1.25 hours between F2 and F3,
this corresponding closely to the measured values.

If the calculations are now performed while providing for a recovery time of 24 hours between flights F1 and F2 and F2 and F3 instead of 30 and 18 hours respectively, and while also keeping the value of d1=7.31 for flight F1, then the mean values at 1 g would have been 6.73 for F2 (instead of 6.60) and 5.59 for F3 (instead of 5.77). Stated otherwise, if the flight F2 is advanced by 6 hours, the value of d is increased for the second flight F2, but it is conversely considerably lowered for the third flight F3.

This is due to the fact that the fatigue rate which switches to 2f after flight F2 is not properly compensated for by the period of rest which is the same between the flights It is therefore beneficial to increase the durations of recovery at the start of the program so as to benefit from the better recovery slope; the r–f slope being more favorable than the r–2f slope where the accumulated fatigue has a negative influence on the recovery.

If it is assumed that the three flights F1, F2, F3 exhibit periods of fatigue at 2 g which are reduced by half, i.e. only 10 minutes in the course of each of the flights, we will then have:

$$f''=f/2=2.15 \times 10^{-3}$$

$$f'''=f2=f=4.3 \times 10^{-3}$$

Keeping the same rate of recovery r and considering a value of d of 7.31 for the first flight F1, we will have mean values at 1 g of 7,03 for a flight F2 performed 30 hours after F1, and 6.48 for the flight F3 performed 18 hours after F2.

This corresponds to a decrease in d of 1% for 8 hours between F1 and F2 and 1% for 2h20 between F2 and F3, this being significantly better than before.

There are therefore two parameters which can be altered, namely the fatigue rate f by modifying the duration of fatigue (phases at 2 g) and the interval between two flights by increasing the recovery time.

Let us take an example in which the number of periods at 2 g is fixed at 30 for each flight $F_1 \ldots F_3$. We need to determine intervals between the flights so as to obtain a relative decrease in the mean values of d at 1 g respectively equal to 5% and 10% after the flights $F_1 \ldots F_2$.

We have r=8.7 $10^{-4}$ and f=4.3 $10^{-3}$.

The interval Δt between the flights F1, and F2 must be such that:

$$(d_1-d_2)/d_1=1-e^{(r-f)\Delta t}=0.05$$

hence $$\Delta t=14.95h \approx 15 \text{ hours}.$$

The interval Δt' between the flights $F_2$ and $F_3$ must be such that:

$$(d_2-d_3)/d_2=1-e^{(r-2f)\Delta t'}=0.1$$

i.e.

Δt=13.6 hours, that is to say 13 h 40 min.

This result may seem paradoxical insofar as, in order to observe a smaller decrease between consecutive flights, the interval between the flights should be shortened, whereas one might logically have considered that longer time intervals would have led to better recovery.

An explanation is that the fatigue rate is much greater than the recovery rate (5 times between $F_1$ and $F_2$ and 10 times between $F_2$ and $F_3$). Therefore the effect of the accumulated fatigue grows as a function of time and the relative decrease continues.

The method according to the invention thus involves various steps:
  the recording of the EEG encephalograms in the course of an exertion sequence and preferably in time intervals of the exertion sequence where the person tested undertakes no exertion;
  the application to these recordings of the known method of the singular attractor or the strange attractor so as to obtain the dimension thereof;
  the optimization of exposure to a stress-inducing environment, as a function of the parameters measured on this person.

This optimization can be performed:
  by increasing or decreasing the period of exposure to a stress-inducing environment;
  and/or by increasing or decreasing the periods of recovery between two periods of exposure to a stress-inducing environment.

This method applies particularly to environments involving a sudden increase in physical stress (exposure to high levels of acceleration, reduced oxygen content, increase in ambient pressure, increase or reduction in ambient temperature) or else to a rapid increase in mental stress (free fall environment, situation of danger, etc.). Such situations are encountered in particular by fighter pilots in the course of acrobatic maneuvers, by astronauts preparing for spacewalks, by professional divers, by free-fall skydivers, or by racing drivers, or more generally during any activity involving exposure to considerable stress for a relatively short duration with respect to the recovery time.

The EEG data can be collected by way of example in the following manner (in conjunction with FIGS. 5a and 5b).

Electrodes are placed in position Fp1, C3 and 01 on the left hemisphere, and Fp2, C4 and 02 on the right hemisphere The signals are recovered on a Micromed twelve-channel recorder having a response between DC and 135 Hz and which has filtering and digitizing means (sampling at 128 Hz). The recordings are made before, during and after the situations of fatigue or intense stress, according to a plan determined in advance and which is tailored to the type of activity analyzed. The data must be gathered over aggregate periods of time of around at least 10 minutes, at least over a cycle of 24 hours.

Preferably, the EEG values are collected:
early in the morning after waking up,
one hour before an exertion sequence,
during the exertion sequence,
one hour after the exertion sequence,
in the evening at the time of going to bed,
next morning on waking up.

The data are transferred to a methodor which calculates the dimensions d of the singular attractors of the EEG signals.

For this purpose, one preferably proceeds in the following manner:

1) avoid any active period so as to record EEG signals only during time intervals of non-activity exhibiting stable alpha waves;
2) calculate the dimensions d over specific time periods;
3) prepare the data files for the calculation algorithm;
4) employ chaos calculation to calculate the dimension of the attractor (method of Babloyantz). An EEG attractor is considered to exist if the curve of d versus n is saturated for $n \leq 10$. In the converse case, the system is considered to be nonconvergent and the corresponding data are discarded;
5) calculate the dimension d of the attractor.

Next, the calculated values of the dimension d and the corresponding time information are input into a processor so as to calculate the characteristic functions according to the exponential model set forth hereinabove.

This function can be used to tailor the intensity of the tasks and/or the interval between tasks for another mission of the same type or of an equivalent type.

Figure 5A:
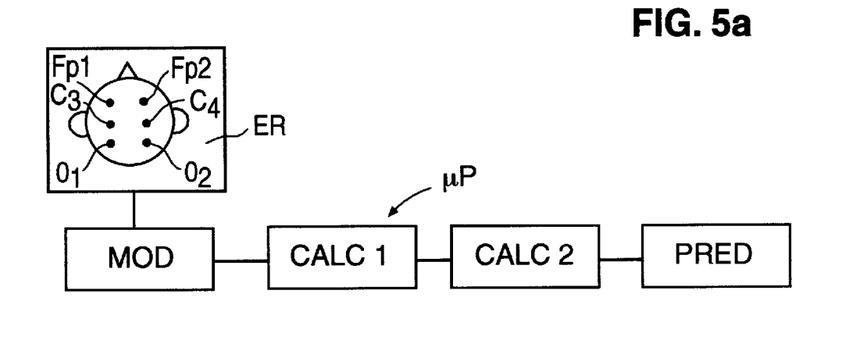
FIGS. 5a and 5b respectively represent an installation for implementing the method and a flowchart relating to the operation thereof.
Figure 5B:
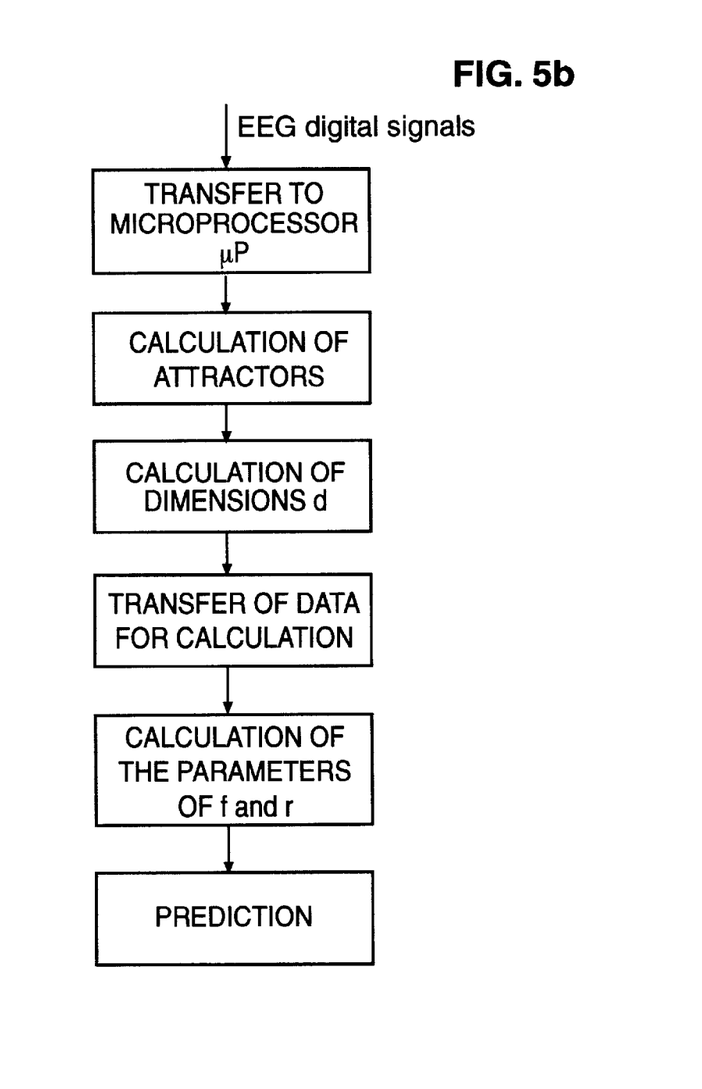

As shown by FIG. 5a, a device for implementing the method involves:

a module MOD for acquiring EEG data;
a module CALC1 for calculating the dimension d of a chaotic attractor, for predefined EEG data series;
a module CALC2 for calculating at least one fatigue coefficient f and a rest coefficient r, from a time-dependent exponential model;
a module PRED for predicting the changes in the dimension d in the course of a sequence comprising at least two rest periods.

The modules MOD, CALC1, CALC2 and PRED advantageously form part of a microprocessor μp, interfaced with the Micromed multichannel recorder EF mentioned hereinabove by way of example (cf. FIG. 5a).

What is claimed is:

1. A method for the predictive determination of a parameter representative of the mental activity of a person, which method involves:

A) the acquisition of encephalograms of said person in the course of at least two exertion sequences separated by a rest sequence;
B) the calculation in the course of each of said exertion sequences of the mean value of the dimension of a chaotic attractor, denoted $d_f(t)$;
C) the calculation for said exertion sequences and said rest sequence of a fatigue function F(t) and of a recovery function R(t) according to an exponential mode, with:

$$F(t)=Fo\ e^{-ft}$$
$$R(t)=Ro\ e^{rt}$$

f and r denoting a fatigue rate, and rest rate respectively;

D) making a prediction df(t) of the changes in the dimension d defined by the product of the fatigue and recovery functions df(t)=F(t)R(t) in the course of at least two exertion sequences having a first and a second durations separated by a period of rest having a third duration.

2. The method as claimed in claim 1, which involves at least two exertion sequences of different intensity and the determination of fatigue coefficients f1, f2, . . . corresponding to each of said sequences.

3. The method as claimed in claim 1, wherein said making of a prediction is carried out by linearly approximating at least one fatigue function and/or the recovery function.

4. The method as claimed in claim 2, wherein said making of a prediction is carried out by linearly approximating at least one fatigue function and/or the recovery function.

5. The method as claimed in claim 1, wherein, in B, the calculation is carried out in respect of encephalograms gathered in time intervals corresponding to exertion sequences and by subsequently comparing them with the encephalograms corresponding to sequences in the course of which said person is not subjected to said exertion.

6. The method as claimed in claim 2, wherein, in B, the calculation is carried out in respect of encephalograms gathered in time intervals corresponding to exertion sequences and by subsequently comparing them with the encephalograms corresponding to sequences in the course of which said person is not subjected to said exertion.

7. The method as claimed in claim 4, wherein, in B, the calculation is carried out in respect of encephalograms gathered in time intervals corresponding to exertion sequences and by subsequently comparing them with the encephalograms corresponding to sequences in the course of which said person is not subjected to said exertion.

8. The method as claimed in claim 1, wherein the making of a prediction involves optimizing the duration of at least one exertion sequence and/or of at least one rest sequence so that after a given time interval, in the course of which several exertion sequences have been carried out, the set of which corresponds to one and the same aggregate exertion alternating with rest sequences, the final value of the dimension d is as large as possible.

9. The method as claimed in claim 2, wherein the making of a prediction involves optimizing the duration of at least one exertion sequence and/or of at least one rest sequence so that after a given time interval, in the course of which several exertion sequences have been carried out, the set of which corresponds to one and the same aggregate exertion alternating with rest sequences, the final value of the dimension d is as large as possible.

10. The method as claimed in claim 4, wherein the making of a prediction involves optimizing the duration of at least one exertion sequence and/or of at least one rest sequence so that after a given time interval, in the course of which several exertion sequences have been carried out, the set of which corresponds to one and the same aggregate exertion alternating with rest sequences, the final value of the dimension d is as large as possible.

11. The method as claimed in claim 7, wherein the making of a prediction involves optimizing the duration of at least one exertion sequence and/or of at least one rest sequence so that after a given time interval, in the course of which several exertion sequences have been carried out, the set of which corresponds to one and the same aggregate exertion alternating with rest sequences, the final value of the dimension d is as large as possible.

12. A device for the predictive determination of parameter representative of the mental activity of a person, which device comprises:
- a module for acquiring encephalographic data;
- a module for calculating the dimension of a chaotic attractor, from the encephalographic data series previously defined;
- a module for calculating at least one fatigue coefficient and a rest coefficient from a time-dependent exponential model of the changes in said dimension;
- a module for predicting the changes in the dimension d in the course of a sequence exhibiting at least two periods of exertion having a first and a second durations separated by a period of rest having a third duration.

13. The device as claimed in claim 12, wherein the second calculation unit has a means of calculating various fatigue coefficients f1, f2, . . . associated with exertion sequences of different intensity.

14. The device as claimed in claim 12, wherein the prediction unit has a subunit making it possible to linearly approximate at least one fatigue function and/or the recovery function.

15. The device as claimed in claim 13, wherein the prediction unit has a subunit making it possible to linearly approximate at least one fatigue function and/or the recovery function.

16. The device as claimed in claim 12, wherein it has an optimization unit making it possible to optimize the duration of at least one exertion sequence and/or of at least one rest sequence so that after a predetermined time interval, in the course of which several exertion sequences have been carried out, the set of which corresponds to one and the same aggregate exertion, alternating with rest sequences, the final value of the dimension d is as large as possible.

17. The device as claimed in claim 13, wherein it has an optimization unit making it possible to optimize the duration of at least one exertion sequence and/or of at least one rest sequence so that after a predetermined time interval, in the course of which several exertion sequences have been carried out, the set of which corresponds to one and the same aggregate exertion, alternating with rest sequences, the final value of the dimension d is as large as possible.

18. The device as claimed in claim 15, wherein it has an optimization unit making it possible to optimize the duration of at least one exertion sequence and/or of at least one rest sequence so that after a predetermined time interval, in the course of which several exertion sequences have been carried out, the set of which corresponds to one and the same aggregate exertion, alternating with rest sequences, the final value of the dimension d is as large as possible.

* * * * *